(12) United States Patent
Rappuoli

(10) Patent No.: US 7,485,304 B2
(45) Date of Patent: *Feb. 3, 2009

(54) NON-TOXIC MUCOSAL ADJUVANT

(75) Inventor: Rino Rappuoli, Quercegrossa (IT)

(73) Assignee: Novartis Vaccines and Diagnostics SRL, Siena (IT)

( * ) Notice: Subject to any disclaimer, the term of this patent is extended or adjusted under 35 U.S.C. 154(b) by 0 days.

This patent is subject to a terminal disclaimer.

(21) Appl. No.: 11/399,571

(22) Filed: Apr. 6, 2006

(65) Prior Publication Data

US 2006/0177469 A1    Aug. 10, 2006

Related U.S. Application Data

(63) Continuation of application No. 10/351,075, filed on Jan. 24, 2003, now Pat. No. 7,070,781, which is a continuation of application No. 09/046,098, filed on Mar. 23, 1998, now abandoned, which is a continuation of application No. 08/646,333, filed as application No. PCT/IB95/00013 on Dec. 22, 1994, now abandoned.

(30) Foreign Application Priority Data

Dec. 22, 1993 (GB) ................................. 9326174.1

(51) Int. Cl.
| | |
|---|---|
| A61K 39/00 | (2006.01) |
| A61K 39/38 | (2006.01) |
| A61K 38/00 | (2006.01) |
| A61K 39/12 | (2006.01) |
| A61K 39/145 | (2006.01) |
| A61K 39/13 | (2006.01) |
| A61K 39/245 | (2006.01) |
| A61K 39/02 | (2006.01) |
| A61K 39/10 | (2006.01) |
| A61K 39/05 | (2006.01) |
| A61K 39/095 | (2006.01) |
| A61K 39/108 | (2006.01) |
| A61K 39/106 | (2006.01) |
| A61K 45/00 | (2006.01) |
| A01N 37/18 | (2006.01) |

(52) U.S. Cl. ............... 424/184.1; 424/265.1; 424/234.1; 424/245.1; 424/264.1; 424/236.1; 424/204.1; 424/254.1; 424/206.1; 424/217.1; 424/261.1; 424/282.1; 424/231.1; 424/250.1; 424/249.1; 424/240.1; 514/2; 514/12

(58) Field of Classification Search .................... None
See application file for complete search history.

(56) References Cited

U.S. PATENT DOCUMENTS

| | | | |
|---|---|---|---|
| 4,328,209 A | 5/1982 | Finkelstein et al. |
| 4,428,931 A | 1/1984 | Tolman et al. |
| 4,666,837 A | 5/1987 | Harford et al. |
| 4,892,827 A | 1/1990 | Pastan et al. |
| 4,925,792 A | 5/1990 | Rappuoli |
| 5,032,398 A | 7/1991 | Kaslow |
| 5,085,862 A | 2/1992 | Klein et al. |
| 5,182,109 A | 1/1993 | Tamura et al. |
| 5,221,618 A | 6/1993 | Klein et al. |
| 5,244,657 A | 9/1993 | Klein et al. |
| 5,332,583 A | 7/1994 | Klein et al. |
| 5,358,868 A | 10/1994 | Klein et al. |
| 5,427,788 A | 6/1995 | Rappuoli et al. |
| 5,433,945 A | 7/1995 | Klein et al. |
| 5,668,255 A | 9/1997 | Murphy |
| 5,747,028 A | 5/1998 | Calderwood et al. |
| 5,770,203 A | 6/1998 | Burnette et al. |
| 5,773,600 A | 6/1998 | Burnette, III |
| 5,785,971 A | 7/1998 | Rappuoli et al. |
| 5,786,189 A | 7/1998 | Locht et al. |
| 5,856,122 A | 1/1999 | Read et al. |
| 5,874,088 A | 2/1999 | Mekalanos |
| 5,874,287 A | 2/1999 | Burnette et al. |
| 5,882,653 A | 3/1999 | Kaper et al. |
| 5,889,172 A | 3/1999 | Pizza et al. |
| 5,908,825 A | 6/1999 | Fasano et al. |
| 5,925,546 A | 7/1999 | Pizza et al. |
| 5,942,418 A | 8/1999 | Loosmore et al. |
| 5,961,970 A | 10/1999 | Lowell et al. |
| 5,965,385 A | 10/1999 | Read et al. |
| 5,977,304 A | 11/1999 | Read et al. |
| 5,985,284 A | 11/1999 | Lowell |

(Continued)

FOREIGN PATENT DOCUMENTS

EP     0396964 A1     11/1990

(Continued)

OTHER PUBLICATIONS

Wu et al, Vaccine, 1998, 16/2-3:286-292.*

(Continued)

Primary Examiner—N. M Minnifield
(74) Attorney, Agent, or Firm—Novartis Vaccines & Diagnostics SRL; Dahna S. Pasternak

(57) ABSTRACT

A non-toxic mucosal adjuvant is provided which may be admixed with further antigens to provide a vaccine administrable to mucosal surfaces in organisms including man. Preferably, the non-toxic mucosal adjuvant is a detoxified mutant of a bacterial ADP-ribosylating toxin, optionally comprising one or more amino acid additions, deletions or substitutions.

7 Claims, 5 Drawing Sheets

U.S. PATENT DOCUMENTS

| | | | |
|---|---|---|---|
| 6,019,982 | A | 2/2000 | Clements |
| 6,030,624 | A | 2/2000 | Russell et al. |
| 6,033,673 | A | 3/2000 | Clements |
| 6,129,923 | A | 10/2000 | Doidge et al. |
| 6,149,919 | A | 11/2000 | Domenighini et al. |
| 6,350,612 | B1 | 2/2002 | Rappouli et al. |
| 6,436,407 | B1 | 8/2002 | Clements et al. |
| 6,440,423 | B1 | 8/2002 | Clements et al. |
| 6,818,222 | B1 | 11/2004 | Rappouli et al. |
| 6,841,155 | B1 | 1/2005 | Barchfeld et al. |
| 6,855,321 | B1 | 2/2005 | Del Guidice et al. |
| 7,056,521 | B2 * | 6/2006 | Barchfeld et al. ........ 424/236.1 |
| 7,070,781 | B2 * | 7/2006 | Rappuoli ................. 424/184.1 |
| 7,115,730 | B1 * | 10/2006 | Pizza et al. ................. 536/23.7 |
| 7,279,169 | B1 * | 10/2007 | Rappuoli et al. ......... 424/236.1 |
| 7,291,588 | B2 * | 11/2007 | Pizza et al. .................... 514/2 |
| 7,384,640 | B1 * | 6/2008 | Holmes et al. ........... 424/201.1 |
| 2001/0018056 | A1 | 8/2001 | Roberts |
| 2002/0044939 | A1 | 4/2002 | Pizza et al. |
| 2002/0187154 | A1 | 12/2002 | Rappouli |
| 2003/0072764 | A1 | 4/2003 | O'Hagan |
| 2003/0113338 | A1 | 6/2003 | Pizza et al. |
| 2003/0170262 | A1 | 9/2003 | Pizza et al. |
| 2003/0176653 | A1 | 9/2003 | Mason et al. |
| 2004/0028690 | A1 | 2/2004 | Rappouli |
| 2004/0109874 | A1 | 6/2004 | Chen et al. |
| 2005/0106178 | A1 * | 5/2005 | O'Hagan ................. 424/209.1 |
| 2005/0106180 | A1 * | 5/2005 | Barchfeld et al. ........ 424/235.1 |
| 2006/0057155 | A1 * | 3/2006 | Masignani et al. ....... 424/190.1 |
| 2006/0159701 | A1 * | 7/2006 | Barchfeld et al. ........ 424/203.1 |
| 2006/0177469 | A1 * | 8/2006 | Rappuoli ................. 424/234.1 |
| 2007/0110809 | A1 * | 5/2007 | Magagnoli et al. .......... 424/486 |

FOREIGN PATENT DOCUMENTS

| | | | |
|---|---|---|---|
| EP | 0462534 | A2 | 12/1991 |
| EP | 0688868 | A1 | 12/1995 |
| WO | WO 92/19265 | A1 | 11/1992 |
| WO | WO 93/13202 | A1 | 7/1993 |
| WO | WO 95/09649 | A1 | 4/1995 |
| WO | WO 95/17211 | A1 | 6/1995 |
| WO | WO 95/34323 | A2 | 12/1995 |
| WO | WO 96/06627 | A1 | 3/1996 |
| WO | WO 99/58145 | A2 | 11/1999 |
| WO | WO 00/18434 | A1 | 4/2000 |
| WO | WO 2006128296 | * | 12/2006 |

OTHER PUBLICATIONS

Lycke, Immunology Letters, 2005, 97:193-198.*
Lomada et al, Vaccine, 2004, 23:555-565.*
Tritto et al, J. Immunology, 2007, 179:5346-5357.*
Takahashi et al, Vaccine, 2006, 24:3591-3598.*
Petrovska et al, Vaccine, 2003, 21:1445-1454.*
Kende et al, Vaccine, 2007, 3219-3227.*
Sanchez et al, JBC, Sep. 6, 2002, 277/36:33369-33377.*
Tebbey et al, Vaccine, 2000, 18:2723-2734.*
O'Hagan et al, Vaccine, 1999, 17:2229-2236.*
Hagiwara et al, Vaccine, 1999, 17:2918-2926.*
Yuki et al, Rev, Med. Virol. 2003, 13:293-310.*
Ugozzoli et al, J. Infectious Diseases, 2001, 183:351-354.*
Holmgren et al, Expert Rev. Vaccines, 2003, 2/2:205-217.*
Douce et al, Vaccine, 1998, 16/11-12:1065-1073.*
Freytag et al, Curr. Top. Microbiol Immunol., 1999, 236:215-36.*
DeMagistris et al, Dev. Biol. Stand. 1998, 92:123-126.*
O'Hagan, J. Pharm. Pharmacol. 1998, 50/1:1-10 (abstract only).*
Anderson, et al., "Immunogens Consisting of Oligosaccharides from the Capsule of Haemophilus Influenzae Type b Coupled to Diphtheria Toxoid or the Toxin Protein CRM197," *J. Clin. Invest.* 76:52-59 (1985).

Anderson, "Antibody Responses To Haemophiles Influenzae Type B And Diptheria Toxin Induced By Conjugates Of Oligosaccharides Of The Type B Capsule With The Nontoxic Protein CRM 197," *Inf. & Immun.* 39(1):233-238 (1983).
Baqar, et al., "Safety And Immunogenicity Of A Prototype Oral Whole-Cell Killed Campylobacter Vaccine Administered With A Mucosal Adjuvant In Non-Human Primates," *Vaccine*, 13(1):22-28 (1995).
Bartley, et al., "Pertussis Holotoxoid Formed in vitro with a Genetically Deactivated S1 Subunit," *PNAS USA* 86:8353-8357 (1989).
Baudner, et al., "The Concomitant Use Of The LTK63 Mucosal Adjuvant And Of Chitosan-Based Delivery System Enhances The Immunogenicity And Efficacy Of Intranasally Administered Vaccines," *Vaccine* 21:3837-3844 (2003).
Bennett, et al., "A Comparison of Commerically Available Adjuvants for Use in Research," *J. Immunol. Methods* 153:31-40 (1992).
Black, et al., "Construction and Characterizations of *Bordetella pertussis* Toxin Mutants," *Infection & Immunity* 55(10):2465-2470 (1987).
Boslego, et al., "Gonorrhea Vaccines," Vaccines and Immunotherapy Chapter 17, pp. 211-223 (1991).
Bowie, et al., "Deciphering the Message in Protein Sequences: Tolerance to Amino Acid Substitutions," *Science* 247:1306-1310 (1990).
Brandtzaeg, "Overview of the Mucosal Immune System," *Current Topics Microbiol. & Immunol.* 146:13-25 (1989).
Burnette, "The Advent of Recombinant Pertussis Vaccines." *Biotechnol.* 8:1002-1005 (1990).
Burnette, *Vaccine Research & Developments* Marcel Dekker Inc., New York, New York (1992).
Burnette, "AB5 ADP-Ribosylating Toxins: Comparative Anatomy and Physiology," *Structure* 2(3):151-158 (1994).
Burnette, et al., "Site-specific mutagenesis of the catalytic subunit of cholera toxin: substituting lysine for Arginine 7 causes loss of activity," Infect. & Immun. 59:4266-4270 (1991).
Carbonetti, et al., "Intracellular Delivery of Cytolytic T-Lymphocyte Epitope Peptide by Pertussis Toxin to Major Histocompatibility Complex Class I Without Involvement of the Cytosolic Class I Antigen Processing Pathway," *Infection & Immunity* 67(2):602-607 (1999).
Chen, "Recent advances in mucosal vaccine development," *J. Controlled Release* 67:117-128 (2000).
Cheng, et al., "The Role Of Camp In Mucosal Adjuvanticity Of *Escherichia coli* Heat-Labile Enterotoxin (LT)," *Vaccine* 18:38-49 (2000).
Clements, et al., "Adjuvant activity of *Escherichia coli* heat-labile enterotoxin and effect on the induction of oral tolerance in mice to unrelated protein antigens," *Vaccine* 6:269-277 (1988).
Communication to EPO Concerning Replacement Claims for Filing with the EPO in Application No. 99922284.7 (2003).
Czerkinsky, et al., "Oral Administration of a Streptococcal Antigen Coupled to Cholera Toxin B Subunit Evokes strong Antibody Responses in Salivary Galnds and Extramucosal Tissues," *Infect. & Immun.* 57:1072-1077 (1989).
de Haan, et al., "Mucosal Immunogenicity of the *Escherichia coli* Heat-Labile Enterotoxin: Role of the A Subunit," *Vaccine* 14(4):260-266 (1996).
de Haan, et al., "Mutational Analysis of the Role of ADP-Ribosylation Activity in the Adjuvant Properties of the *Escherichia coli* Heat-Labile Enterotoxin Towards Intranasally Administered Keyhole Limpet Hemocyanin." *Eur. J. Immunol.* 28:1243-1250 (1998).
Del Giudice, et al., "Genetically Derived Toxoids for use as Vaccines and Adjuvants." *Vaccine* 17:S44-S52 (1999).
Dertzbaugh, et al., "Reduction in Oral Immunogenicity of Cholera Toxin B Subunit by N-terminal Peptide Addition," *Infect & Immun.* 61:384-390 (1993).
Dertzbaugh, et al., "Comparative Effectiveness of the Cholera Toxin B Subunit and Alkaline Phosphatase as Carriers for Oral Vaccines," *Infect & Immun.* 61:48-55 (1993).
Dickinson, et al., "Dissociation Of *Escherichia coli* Heat-Labile Enterotoxin Adjuvanticity From ADP-Ribosyltransferase Activity," *Infect. & Immun.* 63:1617-1623 (1995).

Douce, et al., "Genetically Detoxified Mutants of Heat-Labile Toxin from *Escherichia coli* Are aBle to Act as Oral Adjuvants," *Infection and Immunity* 67(9):4400-4406 (1999).

Douce, et al., "Mutants Of *Escherichia coli* Heat-Labile Toxin Lacking ADP-Ribosyltransferase Activity Act As Nontoxic, Mucosal Adjuvants," *Proc. Natl. Acad. Sci.* 92:1644-1648 (1995).

Douce, et al., "Intranasal Immunogenicity and Adjuvanticity of Site Directed Mutant Derivatives of Cholera Toxin," *Infect Immun* 65:2821-2828 (1997).

Ellis, "New Technologies for Making Vaccines," Chapter 29 pp. 568-575 Vaccines, Plotkin & Mortimer.

Elson, "Cholera Toxin and its Subunits as Potential Oral Adjuvants," *Current Topics Microbiol. & Immunol* 146:29-33 (1989).

Elson, et al., "A Lavage Technique Allowing Repeated Measurement of IgA Antibody in Mouse Intestinal Secretions," *Journal of Immunological Methods* 67:101-108 (1984).

Elson, et al., "Generalized Systemic and Mucosal Immunity in Mice and Mocosal Stimulation with Cholera Toxin," *J. Immunol.* 132:2736-2741 (1984).

Elson, et al., "Cholera Toxin Feeding Did Not Induce Oral Tolerance in Mice and Abrogated Oral Tolerance to an Unrelated Protein Antigen," *The Journal of Immunology* 133(6):2892-2897 (1984).

Elson, et al., "Ir Gene Control of the Murine Secretory IgA Response to Cholera Toxin," *Eur. J. Immunol.* 17:425-428 (1987).

EPO Communication pursuant to Article 96(2) EPC relating to Application EP No. 94928455.8-2116 (2001).

Eriksson, et al., "Recent Advances In Mucosal Vaccines And Adjuvants," *Current Opinion in Immunology* 14:666-672 (2002).

Fontana, et al., "Construction Of Nontoxic Derivatives Of Cholera Toxin And Characterization Of The Immunological Response Against The A Subunit," *Infect. Immun.* 63(6):2356-2360 (1995).

Foss, et al., "Mucosal Immunogenicity And Adjuvanticity Of Cholera Toxin In Swine," *Vaccine* 17:788-801 (1999).

Freytag, et al., "Mucosal Adjuvants," *Vaccine* 23:1804-1813 (2005).

Fujihashi, et al., "A Dilemma For Mucosal Vaccination: Efficacy Versus Toxicity Using Enterotoxin-Based Adjuvants," *Vaccine* 20:2431-2438 (2002).

Giannini, et al., "The Amino-Acid Sequence of Two Non-Toxic Mutants of Diphtherin Toxin: CRM45 and CRM197," *Nucleic Acid Res.* 12(10):4063-4069 (1984).

Giuliani, et al., "Mucosal Adjuvanticity and Immunogenicity of LTR72, a Novel Mutant of *Escherichia coli* Heat-Labile Enterotoxin with Partial Knockout of ADP-ribosyltransferase Activity," *J. Exp. Med.* 187(7):1123-1132 (1998).

Gizurarson, et al., "The Effect of Cholera Toxin and Cholera Toxin B Subunit on the Nasal Mucosal Membrane," *Vaccine* 9:825-832 (1991).

Grant, et al., "Role of Trypsin-Like Cleavage at Arginine 192 in the Enzymatic and Cytotonic Activities of *Escherichia coli* Heat-Labile Enterotoxin," *Infection & Immununity* 62(10):4270-4278 (1994).

Green, Bruce, Curriculum Vitae.

Gupta, et al., "Adjuvants-A Balance Between Toxicity and Adjuvanticity," *Vaccines* 11(13):294-305 (1993).

Hagen, Michael, Curriculum Vitae.

Hagiwar, et al., Effectiveness and Safety of Mutant *Escherichia coli* Heat-Labile Enterotoxin (LT H44A) as an Adjuvant for Nasal Influenza Vaccine. *Vaccine* 19:2071-2079 (2001).

Häse, et al., "Construction and Characterization of Recombinant Vibrio Cholera Strains Producting Inactive Cholera Toxin Analogs," *Infection and Immunity* 62(8):3051-3057 (1994).

Hartman, et al., "Native and Mutant Forms of Cholera Toxin and Heat-Labile Enterotoxin Effectively Enhance Protective Efficacy of Live Attenuated and Heat-Killed Shigella Vaccines." *Infect. Immun.* 67:5841-5847 (1999).

Hazama, et al., "Intranasal Immunization Against Herpes Simplex Virus Infection by using a Recombinant Glycoprotein D Fused with Immunomodulating Proteins, the B Subunit of *Escherichia coli* Heat-Labile Enterotoxin and Interleukin-2." *Immunology* 78:643-649 (1993).

Hirabayashi, et al., "Involvement of Antigen-Presenting Cells in the Enhancement of the In Vitro Antibody Responses by Cholera Toxin B Subunit," *Immunology* 75:493-498 (1992).

Hirabayashi, et al., "Comparison of Intranasal Inoculation of Influenza HA Vaccine Combined With Cholera Toxin B Subunit With Oral or Parenteral Vaccination," *Vaccine* 8:243-248 (1990).

Hirabayashi, et al., "H-2-Unrestricted Adjuvant Effect of Cholera Toxin B Subunit on Murine Antibody Responses to Influenza Virus Haemagglutinin," *Immunology* 72:329-335 (1995).

Hirst, et al., "Cholera Toxin and Related Enterotoxins as Potent Immune Modulators." *J. Appl. Microb. Symp. Suppl.* 48:26S-34S (1998).

Hirst, *The Comprehensive Sourcebook of Bacterial Protein Toxins,* Chapter 6, Academic Press, pp. 104-130, (1999).

Holmgren, et al., "Strategies for the Induction of Immune Responses at Mucosal Surfaces Making Use of Cholera Toxin B Subunit as Immunogen, Carrier, and Adjuvant," *Am. J. Trop. Med. Hyg.* 50(5)Suppl.:42-54 (1994).

Holmgren, et al., "Development of Improved Cholera Vaccine Based on Subunit Toxoid," *Nature* 269:602-604 (1977).

Holmgren, "From Cholera Toxin to Subunit Vaccines," *Current Science* 59(13-14):665-669 (1990).

Holmgren, "Cholera Toxin and Cholera B Subunit as Oral-Mucosal Adjuvant and Antigen Vector Systems," *Vaccine* 11:1179-1184 (1993).

Holmgren, et al., "Mucosal Immunisation And Adjuvants: A Brief Overview Of Recent Advances And Challenges," *Vaccine* 21:S89-S95 (2003).

Hörnquist, et al., "Cholera Toxin Adjuvant Greatly Promotes Antigen Priming to T Cells," European Journal of *Immunology,* 23(9):2136-2143 (1993).

Houghten, "Relative Importance of Position and Individual Amino Acid Residues in Peptide Antigen-Antibody Interactions: Implications in the Mechanism of Antigenic Drivt and Antigenic Shift," *Vaccines* 86:21-25 (1986).

Jakobsen, et al., "Intranasal Immunization with Pneumococcal Polysaccharide Conjugate Vaccines with Nontoxic Mutants of *Escherichia coli* Heat-Labile Enterotoxins as Adjuvants Protects Mice Against Invasive Pneumococcal Infections," *Infection and Immunity* 67(11):5892-5897 (1998).

Kang, et al., "Expression Of Non-Toxic Mutant Of *Escherichia coli* Heat-Labile Enterotoxin In Tobacco Chloroplasts," *Protein Expression and Purification* 38:123-128 (2004).

Kaslow, H.R. et al., "Effects of Site-Directed Mutagenesis on Cholera Toxin A1 Subunit ADP-Ribosytransferase Activity," 92nd Gen. Meet. Am. Soc. Microbiol., 1992, Anstract B291, 74.

Kikuta, et al., "Cross-Protection Against Influenza B type Virus Infection by Intranasal Inoculation of the HA Vaccines Combined with Cholera Toxin B Subunit," *Vaccine* 8:594-599 (1990).

Langer, "New Methods of Drug Delivery," *Science* 249:1527-1533 (1990).

Lebman, et al., "Intraduodenal Application of Cholera Holotoxin Increases the Potential of Clones from Peyer's Patch B Cells of Relevant and Unrelated Specificities to Secrete IgG and IgA," *Regional Immun.* 1:32-40 (1988).

Lemere, et al., "Intranasal Immunotherapy For The Treatment Of Alzheimer's Disease: *Escherichia coli* LT And LT(R192G) As Mucosal Adjuvants," *Neurobiology of Aging* 23:991-1000 (2002).

Liang, et al., "Oral Administration of Cholera Toxin-Sendai Virus Conjugate Potentiates Gut and Respiratory Immunity Against Sendai Virus," *J. Immunol.* 141(5):1495-1501 (1988).

Lobet, et al., "Effect of Site-Directed Mutagenic Alterations of ADP Ribosyltransferase Activity of the A Subunit of *Escherichia coli* Heat-Labile Enterotoxin," *Infect. & Immun.,* 59:2870-2879 (1991).

Loosmore, et al., "Engineering of Genetically Detoxified Pertussis Toxin Analogs for Development of a Recombinant Whooping Cough Vaccine," *Infect Immun.* 58(11):3653-3662 (1990).

Losonsky, et al., "B Cell Responses In Gastric Antrum And Duodenum Following Oral Inactivated Helicobacter Pylori Whole Cell (HWC) Vaccine And LT(R192G) In H Pylori Seronegative Individuals," *Vaccine* 21:562-565 (2003).

Lycke, et al., "The Adjuvant Effect of *Vibrio cholerae* and *Escherichia coli* Heat-Labile Enterotoxins is Linked to Their ADP-Ribosyltransferase Activity," *Eur. J. Immunol.,* 22:2277-2281 (1992).

Lycke & Holgren, "Strong Adjuvant Properties of Cholera Toxin on Gut Mucosal Immune Responses to Orally Presented Antigens," *Immunology* 59:301-308 (1986).

Lycke, et al, "The Mechanism of Cholera Toxin Adjuvanticity." *Res. Immunol.* 198:504-520 (1997).

Magagnoli, et al., "Mutations in the A subunit affect yield, stability, and protease sensitivity of nontoxic derivatives of heat-labile enterotoxin," *Infect & Immun.* 64:5434-5438 (1996).

Marchetti, et al., "Protection Against Helicobacter pylori Infection in Mice by Intragastric Vaccination with H. pylori Antigens is Achieved Using a Non-Toxic Mutant of *E. coli* Heat-Labile Enterotoxin (LT) as Adjuvant," *Vaccine* 16(1):33-37 (1998).

Martindale, *Royal Pharmaceutical Society of Britain* Pharmaceutical Press, London, England, pp. 1277-1304(1993).

Matousek, et al., "Distinct Effects of Recombinant Cholera Toxin B Subunit and Holotoxin on Different Stages of Class II MHC Antigen Processing and Presentation by Macrophages," *J. Immunol.* 156:4137-4145 (1996).

McKenzie, et al., "Cholera Toxin B Subunit as a Carrier Protein to Stimulate a Mucosal Immune Response," *J. Immunol.* 133(4):1818-1824 (1984).

McCluskie, et al., "Mucosal Immunization Of Mice Using Cpg DNA And/Or Mutants Of The Heat-Labile Enterotoxin Of *Escherichia coli* As Adjuvants," *Vaccine* 19:3759-3768 (2001).

"Multicomponent Vaccine Development" *NIH Guide* vol. 22, No. 28 (1993).

Nicollier-Jamot, et al., "Recombinant Virus-Like Particles Of A Norovirus (Genogroup II Strain) Administered Intranasally And Orally With Mucosal Adjuvants LT And LT(R192G) In BALB/C Mice Induce Specific Humoral And Cellular Th1/Th2-Like Immune Responses," *Vaccine* 22:1079-1086 (2004).

O'Hagan, et al., "Recent Developments In Adjuvants For Vaccines Against Infectious Diseases," *Biomolecular Engineering*, 18:69-85 (2001).

Okamoto, et al., "Effect of Subtitution of Glycine for Arginine at Position 146 of the A1Subunit of Biological Activity of *Escherichia coli* Heat-Labile Enterotoxin," *J. Bacteriol.* 170(5):2208-2211 (1988).

Ott, et al., in: Vaccine Design: The Subunit & Adj. Approach eds. Powell et al. pp. 277-295 1995.

Periwal, et al., "A Modified Cholera Holotoxin CT-E29H Enhances Systemic And Mucosal Immune Responses To Recombinant Norwalk Virus-Virus Like Particle Vaccine," *Vaccine* 21:376-385 (2003).

Pierce, "The Role of Antigen Form and Function in the Primary and Secondary Intestinal Immune Responses to Cholera Toxin and Toxoid in Rats," *J. Exp. Med.* 148:195-206 (1978).

Pierce, et al., "Cellular Kinetics of the Intestinal Immune Response to Cholera Toxoid in Rats," *J. Exp. Med.* 142:1550-1563 (1975).

Pierce, et al., "Procholeragenoid: A Safe and Effective Antigen for Oral Immunization Against Experimental Cholera," *Infection and Immunity* 40(3):1112-1118 (1963).

Pizza, et al., "Mucosal Vaccines: Non Toxic Derivatives Of LT And CT As Mucosal Adjuvants," *Vaccine* 19:2534-2541 (2001).

Quere, et al., "Systemic Adjuvant Effect Of Cholera Toxin In The Chicken," *Vet. Immunology and Immunopathology*, 70:135-141.

Rappuoli, et al., "Genetic Detoxification of Bacterial Toxins: A New Approach to Vaccine Development," *Inter. Arch. Allergy & Immunol.* 108:327-333 (1995).

Rappouli, et al., "Structure and Mucosal Adjuventicity of Cholera and *Escherichia coli* Heat-Labile Enterotoxins." *Immunol. Today* 20:493-500 (1999).

Roberts, et al., "A mutant pertussis toxin molecule that lacks ADP-ribosyltransferase activity, PT-9K/129G, is an effective mucosal adjuvant for intranasally delivered proteins," *Infect. & Immun.* 63:2100-2108 (1995).

Rodighiero et al., "Structural basis for the differential toxicity of cholera toxin and *Escherichia coli* heat-labile enterotoxin,," *J. Biol. Chem.* 274(7):3962-3969 (1999).

Sanchez, et al., "Recombinant Cholera Toxin B Subunit and Gene Fusion Proteins Oral Vaccination," *Res. Microbiol.* 141:971-979 (1990).

Scharton-Kersten, et al., "Principles Of Transcutaneous Immunization Using Cholera Toxin As An Adjuvant," *Vaccine* 17:S37-S43 (1999).

Snider, "The Mucosal Adjuvant Activities of ADP-Ribosylating Bacterial Enterotoxins," *Crit. Rev. Immunol.* 15:317-348 (1995).

Sougioultzis, et al., "Safety And Efficacy Of *E coli* Enterotoxin Adjuvant For Urease-Based Rectal Immunization Against Helicobacter Pylori," *Vaccine* 21:194-201 (2002).

Spangler, "Structure and Function of Cholera Toxin and The Related *Escherichia coli* Heat-Labile Enterotoxin" *Microbiol. Rev.* 56:622-647 (1992).

Streatfield, et al., "Intermolecular Interactions Between the A and B Subunits of Heat-Labile Enterotoxin from *Escherichia coli* Promote Holotoxin Assembly and Stability in vivo," *Proc. Natl. Acad. Sci. U.S. A.* 89:12140-12144 (1992).

Sultzer, et al., "The Adjuvant Effect of Pertussis Endotoxin Protein in Modulating the Immune Response to Cholera toroid in Mice," *Proceedings of the Fourth Intl. Symposium on Pertussis, Joint IABS/WHO Meeting, Geneva Switzerland, 1984 Develop. in biol. Stand.* 61:225-232 (1985).

Takahashi, et al., "Mechanisms For Mucosal Immunogenicity And Adjuvancy Of *Escherichia coli* Labile Enterotoxin," *J. Infectious Diseases* 173:627-635 (1996).

Tamura, et al., "Cross-Protection Against Influenza Virus Infection Afforded By Trivalent Inactivated Vaccines Inoculated Intranasally with Cholera Toxin B Subunit," *The Journal Immunology* 149(3):981-988 (1992).

Tamura, et al., "Enhancement of Protective Antibody Responses by Cholera Toxin B subunit Inoculated Intranasally With Influenza Vaccine," *Vaccine* 7:257-262 (1989).

Tamura, et al. "Protection Against Influenza Virus Infection by Vaccine Inoculated Intranasally With Cholera Toxin B Subunit," *Vaccine* 6:409-413 (1988).

Tamura, et al., "Protection Against Influenza Virus Infection by a Two-Dose Regimen of Nasal Vaccination Using Vaccines Combined With Cholera Toxin B Subunit," *Vaccine* 7:314-320 (1989).

Tamura, et al., "Effectiveness of Cholera Toxin B Subunit as an Adjuvant for Nasal Influenza Vaccination Despite Pre-Existing Immunity to CTB," *Vaccine* 7:503-505 (1989).

*The Comprehensive Sourcebook of Bacterial Protein Toxins*, 2$^{nd}$ Ed., Academic Press, pp. 696-697.

Torres, et al., "Clostridium Difficile Vaccine: Influence of Different Adjuvants and Routes of Immunization on Protective Immunity in Hamsters," *Vaccine Research* 5(3):149-162 (1996).

Tommaso, et al., "Induction of antigen-specific antibodies in vaginal secretions by using a nontoxic mutant of heat-labile enterotoxin as a mucosal adjuvant," *Infect. & Immun.* 64:974-979 (1996).

Tsuji, et al., "A single amino acid substitution in the A subunit of *Escherichia coli* enterotoxin results in a loss of its toxic activity," *J. Biol. Chem.* 265:22520-22525 (1990).

Tsuji, et al., "Relationship Between a Low Toxicity of the Mutant A Subunit of Enterotoxigenic *Escherichia coli* Enterotoxin and its Strong Adjuvant Action." *Immunology* 90:176-182 (1997).

Vadolas, et al., "Intranasal Immunization with Liposomes Induces Strong Mucosal Immune Responses in Mice," *Eur. J. Immunol.* 25:969-975 (1995).

Van den Akker, et al., "The Arg7Lys Mutant of Heat-Labile Enterotoxin Exhibits Great Flexibility of Active Site Loop 47-56 of the A Subunit," *Biochemistry* 34:10996-1104 (1995).

Verweij, et al., "Musosal Immunoadjuvant Activity of Recombinant *Escherichia coli* Heat-Labile Enterotoxin and Subunit: Induction of Systemic IgG and Secretory IgA Responses in Mice by Intranasal Immunization with Influenza Virus Surface Antigen," *Vaccine* 16(20):2069-2076 (1998).

Walker, et al.. "Use of Heat-Labile Toxin of Enterotoxigenic *Escherichia coli* to Facilitate Mucosal Immunization," *Vaccine Res.* 2(1):1-10 (1993).

Warren, et al., "Current status of immunological adjuvants," *Ann. Rev. Immun.* 4:369-388 (1986).

Watanabe, et al., "Characterization Of Protective Immune Responses Induced By Nasal Influenza Vaccine Containing Mutant Cholera Toxin As A Safe Adjuvant (CT112K)," *Vaccine* 20:3443-3455 (2002).

Williams, Affidavit, Curriculum Vitae, and Annex I.

Yamamoto, et al., "Mutants in the ADP-Ribosyltransferase Cleft of Cholera Toxin Lack Diarrheagenicity but Retain Adjuvanticity," *J. Exp. Med.* 185:1203-1210 (1997).

Yokomizo, et al., "Mucosal Immunoadjuvant Activity Of The Low Toxic Recombinant *Escherichia coli* Heat-Labile Enterotoxin Produced By Bacillus Brevis For The Bacterial Subunit Or Component Vaccine In Pigs And Cattle," *Vet. Immunology and Immunopathology* 87:291-300 (2002).

* cited by examiner

FIG. 1b

Legend:
- Pre-immune sera
- Day 21
- Day 35
- Day 56
- Day 76

Detection Limit 1:50

* Sera not tested

Groups (x-axis): CT+Ova I/N, LT+Ova I/N, LT K7+Ova I/N, Ova Alone I/N, CT+Ova S/C, LT+Ova S/C, LT K7+Ova S/C, Ova Alone S/C Y-axis: ELISA Titre of toxin specific antibodies (10, 100, 1000, 10000)

NON-TOXIC MUCOSAL ADJUVANT

CROSS REFERENCE TO RELATED APPLICATIONS

This application is a continuation of application Ser. No. 10/351,075 filed Jan. 24, 2003, now U.S. Pat. No. 7,070,781, which is a continuation of application Ser. No. 09/046,098 filed Mar. 23, 1998, now abandoned, which is a continuation of application Ser. No. 08/646,333 filed Jun. 5, 1996, now abandoned, which is a U.S. national phase application of PCT/IB95/00013 filed Dec. 22, 1994 claiming priority of PCT/IB94/00068 filed Mar. 24, 1994 and Great Britain Serial No. 9326174.1 filed Dec. 22, 1993, from which application(s) priority is claimed pursuant to 35 U.S.C. §120 and which applications are herein incorporated by reference in their entireties.

FIELD OF THE INVENTION

The present invention relates to an adjuvant useful for the administration of vaccines to organisms. In particular, the adjuvant of the invention allows the delivery of vaccines to mucosal surfaces to raise a secretory and systemic immune response.

BACKGROUND OF THE INVENTION

Current vaccination technology is based almost exclusively on systemic vaccination techniques wherein the vaccine is injected into the subject to be vaccinated. Only certain live/attenuated vaccines, such as Sabin polio vaccine, may be taken orally.

The advantages of oral immunization techniques are several fold. For instance, it is self-evident that a vaccine which may be fed to subjects is easier to administer on a large scale in the absence of specialized equipment, especially to subjects which may be difficult to handle or even locate, such as livestock and wild animals. The spread of infection by the re-use of needles in developing countries would thereby be avoided. Furthermore, an oral vaccine may be provided in the form of an edible solid, which is easier to handle under extreme conditions and is more stable than the liquid suspensions as currently used.

Moreover, delivery of immunogens to a mucosal membrane, such as by oral or intranasal vaccination, would permit the raising of a secretory immune response.

The secretory immune response, mainly Iga-mediated, appears to be substantially separate from a systemic immune response. Systemic vaccination is ineffective for raising a secretory immune response. This is a considerable disadvantage when considering immunization against pathogens, which often enter the subject across a mucosal surface such as the gut or lung.

Unfortunately, it is not possible to raise a secretory immune response to the vast majority of antigens simply by exposing mucosal surfaces to such antigens. Furthermore, no adjuvant capable of eliciting a secretory immune response to a given antigen is currently available.

The apparent difficulty is largely due to a phenomenon known as oral tolerance. The linings of the gut and the lungs are naturally tolerant to foreign antigens, which prevents an immune response being raised to ingested or inhaled substances, such as food and airborne particulate matter.

The ADP-ribosylating bacterial toxins, namely diphtheria toxin, pertussis toxin (PT), cholera toxin (CT), the *E. coli* heat-labile toxin (LT1 and LT2), *Pseudomonas* endotoxin A, *C. botulinum* C2 and C3 toxins as well as toxins from *C. perfringens*, *C. spiriforma* and *C. difficile* are potent toxins in man. These toxins are composed of a monomeric, enzymatically active A subunit which is responsible for ADP-ribosylation of GTP-binding proteins, and a non-toxic B subunit which binds receptors on the surface of the target cell and delivers the A subunit across the cell membrane. In the case of CT and LT, the A subunit is known to increase intracellular cAMP levels in target cells, while the B subunit is pentameric and binds to GM1 ganglioside receptors.

In 1975 and 1978 observations were made which demonstrated that CT is able to induce mucosal and systemic immunity against itself when administered intraduodenally (i.e. to a mucosal surface). The membrane-binding function of CT was shown to be essential for mucosal immugenicity, but cholera toxoid, also known as the B subunit of CT (CTB) was inactive in isolation (Pierce and Gowans, J. Exp. Med 1975; 142: 1550; Pierce, J. Exp Med 1978; 148: 195-206).

Subsequently, it was demonstrated that CT induces systemic and mucosal immunity to co-administered antigens, in other words functions as a mucosal adjuvant (Elson, Curr. Top. Microbiol. Immunal, 1989; 146: 29; Elson and Ealding, J. Immunol. 1984; 133: 2892-2897; Elson and Ealding, Ibid. 1984; 132: 2736-2741; Elson et al., J. Immunol. Methods 1984; 67: 101-118; Lycke and Homgren, Immunology 1986; 59: 301-338).

The experiments referred to above were conducted in mice, which are comparatively resistant to the toxic effects of CT. In contrast, wild-type CT is extremely toxic to humans, rendering the use of CT having any substantial residual toxicity as a mucosal adjuvant in humans entirely out of the question.

Two approaches have been taken in the prior art to address the problem of CT toxicity. The first approach has involved the use of CTB as a mucosal adjuvant. CTB is entirely non-toxic.

In one series of experiments, CTB was covalently coupled to horseradish peroxidase (HRP) and administered to mice intraduodenally. This gave rise to a powerful mucosal immune response to HRP (McKenzie and Halsey, J. Immunol 1984; 133: 1818-1824).

This result has subsequently been partially confirmed with other antigens (Liang et al., J. Immunol 1988; 141: 1495-1501; Czerkinsky et al., Infect. Immun. 1989; 57: 1072-1077). The same principle has also been established to be effective when chimeric antigens produced by gene fusion to sequences encoding CTB have been tested (Dertzbaugh and Elson, Infect. Immun. 1993; 61: 384-390; Dertzbaugh and Elson, Ibid. 1993; 61: 48-55; Sanchez et al., Res. Microbiol 1990; 141: 971-979; Holmgren et al., Vaccine 1993; 11: 1179-1184).

However, the production of chimeric or coupled antigens introduces a further step in the preparation of suitable vaccines, which essentially requires that antigens be prepared in a form conjugated with CTB especially for oral use. It would be for simpler and more economical if the adjuvant could be administered in simple admixture with the antigen.

An adjuvant effect for co-administered CTB has been alleged in a number of publications (Tamura et al., J. Immunol 1992; 149: 981-988; Hirabayashi et al., Immunology 1992; 75: 493-498; Gizurarson et al., Vaccine 1991; 9: 825-832; Kikuta et al., Vaccine 1970; 8: 595-599; Hirabayashi et al. Ibid. 1990; 8; 243-248; Tamura et al., Ibid. 1989; 7: 314-32-; Tamura et al., Ibid. 1989; 7: 257-262; Tamura et al., Ibid 1988; 6: 409-413; Hirabayashi et al., Immunology 1991; 72: 329-335 Tamura et al., Vaccine 1989; 17: 503-505).

However, a number of aspects of the observations reported above were not entirely convincing. For example, it was noted that the adjuvant effect ascribed to CTB was not H-2 restricted. It is known, however, that immune response to CTB is H-2 restricted (Elson and Ealding, Eur. J. Immunol. 1987; 17: 425-428). Moreover, the alleged adjuvant effect was observed even in individuals already immune to CTB.

Other groups were unable to observe any mucosal adjuvant effect attributable to CTB (Lycke and Holmgren, Immunology 1986; 59: 301-308; Lycke et al., Eur. J. Immunol. 1992; 22: 2277-2281). Experiments with recombinant CTB (Holmgren et al., Vaccine 1993; 11: 1179-1183) confirmed that the alleged effect is largely if not exclusively attributable to low levels of contamination of CTB preparations with CT.

Thus, it is presently accepted that CTB is not useful as a mucosal adjuvant.

A second approach to eliminating the toxicity of CT has been to mutate the CT holotoxin in order to reduce or eliminate its toxicity. The toxicity of CT resides in the A subunit and a number of mutants of CT and its homologue, LT, comprising point mutations in the A subunit are known in the art. See, for example, International Patent Application WO92/19265 (Amgen). It is accepted in the art that CT and LT are generally interchangeable, showing considerable homology.

However, the only mutant so far tested for mucosal adjuvanticity, an LT mutant having a Glu→Lys mutation at position 112, was found to be inactive as a mucosal adjuvant (Lycke et al; Eur. J. Immunol. 1992; 22: 2277-2251; Holmgren et al., Vaccine 1993; 11: 1179-1183). The authors of these publications conclude that there is a link between the ADP ribosylating activity of CT and/or LT and the adjuvant activity. It appears from these publications, therefore, that CTB or a non-toxic mutant of CT or LT would not be active as a mucosal adjuvant.

SUMMARY OF THE INVENTION

There therefore remains a need for an active mucosal adjuvant which may be used to increase the immunogenicity of an antigen when administered to a mucosal surface, such as orally or intranasally.

It has now been discovered that, in complete contradiction with the results and conclusions presented in the prior art, the toxic and adjuvant activities of the ADP-ribosylating toxins are separable. An entirely non-toxic mutant of such a toxin has been shown to be active as a mucosal adjuvant.

The present invention, in a first aspect, provides a pharmaceutical composition comprising a non-toxic mucosal adjuvant in admixture with a second antigen.

It has been demonstrated that an LT mutant which completely lacks toxicity is active as a mucosal adjuvant and protects subjects against subsequent challenge with a lethal dose of the immunogen. Although the Applicants do not wish to be bound by any particular theory, it is postulated that the results of Lycke et al. and Holmgren et al. quoted above may be contradicted at least in part because they fail to take into account the stability of the mutant being made. Inter alia by ensuring that the non-toxic mutant of the invention is stable at the site of delivery, it has been demonstrated that the adjuvant effect of CT and/or LT may be maintained while its toxic effects are eliminated.

Preferably, therefore, the non-toxic mucosal adjuvant is a detoxified mutant of a bacterial ADP-ribosylating toxin, optionally comprising one or more amino acid additions, deletions or substitutions.

Particularly suitable are detoxified mutants of CT or LT. For example, a mutant LT in accordance with the invention may possess an Arg7 to Lys7 substitution at position 7 of the A subunit, the so-called LTK7 mutant.

Alternative mutants are known to those skilled in the art and are preferred molecules for use in the present invention. Examples include PT mutated at position 129, in particular PT having a Glu 129->Gly mutation. Further mutants include PT mutated at one or both of Trp 26 and Arg 9, optionally in combination with the Glu 129 mutation.

The mutant used in the invention may moreover be a mutant wherein the mutation has been effected in a part of the molecule which results in the prevention of proteolytic cleavage of the A subunit of the toxin, such that enzymatic activity is not brought about. Such mutants are described in Grant et al. Inf. and Immunity (1994) 62(10) 4270-4278. For example, the mutant may comprise an Arg 192->Gly mutation in LT or a corresponding mutation in another ADP-ribosylating toxin.

The mutant of the invention is preferably in the form of a holotoxin, comprising the mutated A subunit and the B subunit, which may be oligomeric, as in the wild-type holotoxin. The B subunit is preferably not mutated. However, it is envisaged that a mutated A subunit may be used in isolation from the B subunit, either in an essentially pure form or complexed with other agents, which may replace the B subunit and/or its functional contribution.

Methods for the design and production of mutants of CT and/or LT are known in the art. Suitable methods are described in International Patent Application WO93/13202 (Biocine Sclavo), the disclosure of which is incorporated herein by reference, as well as WO92/19265 (Amgen).

The adjuvant of the invention is preferably administered in admixture with a suitable antigen against which it is desired to raise an immune response. If the antigen and the adjuvant are not in admixture, it is preferred that they be administered within a relatively short time of each other, at the same site of administration. It has been observed that the adjuvant effect provided by wild-type CT is short lived (see Lycke and Homgren, Immunology 1986; 59: 301-308). In an alternative embodiment, the mucosal adjuvant of the invention may be administered, optionally in isolation from other antigens, as a boost following systemic or mucosal administration of a vaccine.

The precise formulation of the vaccine may vary in accordance with the nature of the immunogen. For example, if the antigen is enclosed in slow-releasing microspheres to liposomes, the mucosal adjuvant may be similarly enclosed so that the antigen and the adjuvant may interact simultaneously with the mucosal immune system. Alternatively, separate mucosal administration of the adjuvant of the invention may be used to enhance mucosal response to parentally-administered vaccines.

In a second aspect, the present invention provides the use of a non-toxic mutant of CT or LT as a mucosal adjuvant in the preparation of a composition for mucosal administration.

Preferably, the composition is a vaccine and is useful for the immunisation of a subject against a disease or the treatment of a subject suffering from a disease.

Preferably, the mutant comprises one or more amino acid additions, substitutions or deletions in the amino acid sequence of the A subunit of CT or LT which is or are effective to abolish the toxicity of the toxin.

According to a third aspect of the invention, there is provided a method for the prevention or treatment of a disease in a subject comprising administering to the subject an immunologically effective dose of an antigen adjuvanted with a non-toxic CT or LT mutant by contacting a mucosal surface of the subject with said adjuvanted antigen.

The mucosal surface may be any suitable mucosal surface of the subject. For example, the administration may be carried out by inhalation, by means of a rectal or vaginal suppository, or a pessary, by feeding or other buccal administration, by means of an aerosol, by intranasal delivery or direct application to mucosal surfaces. Especially preferred are oral and intranasal administration.

The subject may be any organism susceptible to immunisation. Especially indicated are humans and other mammals such as livestock, pets and wildlife.

Diseases against which the subject may be immunised include all diseases capable of being treated or prevented by immunisation, including viral diseases, allergic manifestations, diseases caused by bacterial or other pathogens which enter through or colonise mucosal surfaces, AIDS, autoimmune diseases such as systemic Lupus Erythe—matosus, Alzheimer's disease and cancers. Examples of viral infections which may be treated or prevented using the invention include infection by DNA viruses, such as EBV and VZV, and in particular herpesviridae, for example HSV and HCMV, adenoviridae, papovaviridae, such as HPV, hepadnaviridae, such as HBV, infection by RNA viruses, such as picorvaviridae, especially polivirus and HAV, rhinoviruses and FMDV, togaviridae, flaviviridae, coronaviridae, paramyxoviridae, such as RSV, orthomyxoviridae, such as influenza virus, and retroviridae, especially HIV. Vaccination against HCV and HDV is also envisaged.

Examples of bacterial infections suitable for treatment or prophylaxis by the invention include infection with *Helicobacter pylori, streptococci, meningococcus* A, B, and C, *bordetella pertussis* and chlamydia and trachomatis.

Vaccine formulation suitable for delivery at mucosal surfaces may be prepared as set out hereinbelow, while further formulations will be apparent to those of skill in the art. Suitable administration regimes are, likewise, set out below while modifications of the exemplified values will be apparent to those of skill in the art.

Moreover, the invention provides a mutant of CT or LT which is a non-toxic mucosal adjuvant and a second antigen for simultaneous separate or sequential administration. Simultaneous administration of the adjuvant and the second antigen when combined in a single vehicle, carrier or particle, as exemplified below, is particularly preferred.

The second antigen may be any antigen to which it is desired to raise an immune response in the subject. Suitable antigens comprise bacterial, viral and protozoan antigens derived from pathogenic organisms, as well as allergens, allogens and antigens derived from tumours and self-antigens. Typically, the antigen will be a protein, polypeptide or peptide antigen, but alternative antigenic structures, such as nucleic acid antigens, carbohydrate antigens, and whole or attenuated or inactivated organisms such as bacteria, viruses or protozoa are not excluded. The invention further provides a method for the manufacture of an adjuvanted vaccine comprising the steps of:

a) performing site-diected mutagenesis on the A-subunit of a bacterial ADP-ribosylating toxin in order to detoxify the toxin; and
b) bringing the detoxified toxin into association with a second antigen, such that it functions as a mucosal adjuvant.

Specific examples of antigens useful in the present invention include HSV gD, gB and other glycoproteins; HIV gp120 and other proteins; CMV gB or gH; HCV antigens; HDV delta antigen; HAV antigens; EBV and VZV antigens; *B. pertussis* antigens and *H. pylori* antigens.

In general, the second antigen may be the immunogenic component of the vaccine intended for injection. Such vaccines, and the immunogenic components thereof, may be subunit vaccines, whole inactivated or attenuated organisms or polynucleotide vaccines.

The vaccines according to the invention may either be prophylactic (to prevent infection) or therapeutic (to treat disease after infection).

These vaccines may either be prophylactic (to prevent infection) or therapeutic (to treat disease after infection).

Such vaccines comprise antigen or antigens, usually in combination with "pharmaceutically acceptable carriers," which include any carrier that does not itself induce the production of antibodies harmful to the individual receiving the composition.

Suitable carriers are typically large, slowly metabolized macromolecules such as proteins, polysaccharides, polylactic acids, polyglycolic acids, polymeric amino acids, amino acid copolymers, lipid aggregates (such as oil droplet emulsions or liposomes), and inactive virus particles. Such carriers are well known to those of ordinary skill in the art. In preferred aspects of the invention, these carriers may function as immunostimulating agents ("adjuvants"). Furthermore, the antigen may be conjugated to a bacterial toxoid, such as a toxoid from diphtheria, tetanus, cholera, *H. pylori*, etc. pathogens.

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (PCT Publ. No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110y microfluidizer (Microfluidics, Newton, Mass.), (b) SAP, containing 10% Squalane, 0.4% Tween 80, 5% pluronic-blocked polymer L121, and thr-MDP (see below) either microfluidized into a submicron emulsion or vortexed to generate a larger particle size emulsion, and (c) RIBI™ adjuvant system (RAS), (Ribi Immunochem, Hamilton, Mo.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (DETOX™); (3) saponin adjuvants, such as STIMULON™ (Cambridge Bioscience, Worcester, Mass.) may be used or particles generated therefrom such as ISCOMs (immunostimulating complexes); (4) Complete Freunds Adjuvant (CFA) and Incomplete Freunds Adjuvant (IFA); (5) cytokines, such as interleukins (e.g., IL-1, IL-2, IL-4, IL-5, IL-6, IL-7, IL-12, etc.), interferons (e.g., gamma interferon), macrophage colony stimulating factor (M-CSF), tumor necrosis factor (TNF), etc; and (6) other substances that act as immunostimulating agents to enhance the effectiveness of the composition. Alum and MF59 are preferred.

As mentioned above, muramyl peptides include, but are not limited to, N-acetyl-muramyl-L-threonyl-D-isoglutamine (thr-MDP),N-acetyl-normuramyl-l-alanyl-d-isoglutamine (nor-MDP),N-acetylmuramyl-l-alanyl-d-isoglutaminyl-l-alanine-2-(1'-2'-dipalmitoyl-sh-glycero-3-huydroxyphosphoryloxy)-ethylamine (MTP-PE), etc.

The immunogenic compositions (e.g., the antigen, pharmaceutically acceptable carrier, and adjuvant) typically will contain diluents, such as water, saline, glycerol, ethanol, etc.

Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (e.g., nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, e.g., by injection, either subcutaneously or intramuscularly. Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents.

Examples of suitable immunostimulatory agents include interleukins, such as interleukins 1,2, 4-7 and 12, and interferons, especially γ-interferon.

The invention is described hereinbelow by way of example only, with reference to the following Figures:

DESCRIPTION OF THE FIGURES

FIG. 1b shows the titre of total toxin-specific antibody in the mice of FIG. 1a;

DETAILED DESCRIPTION OF THE INVENTION

Figure 1A:
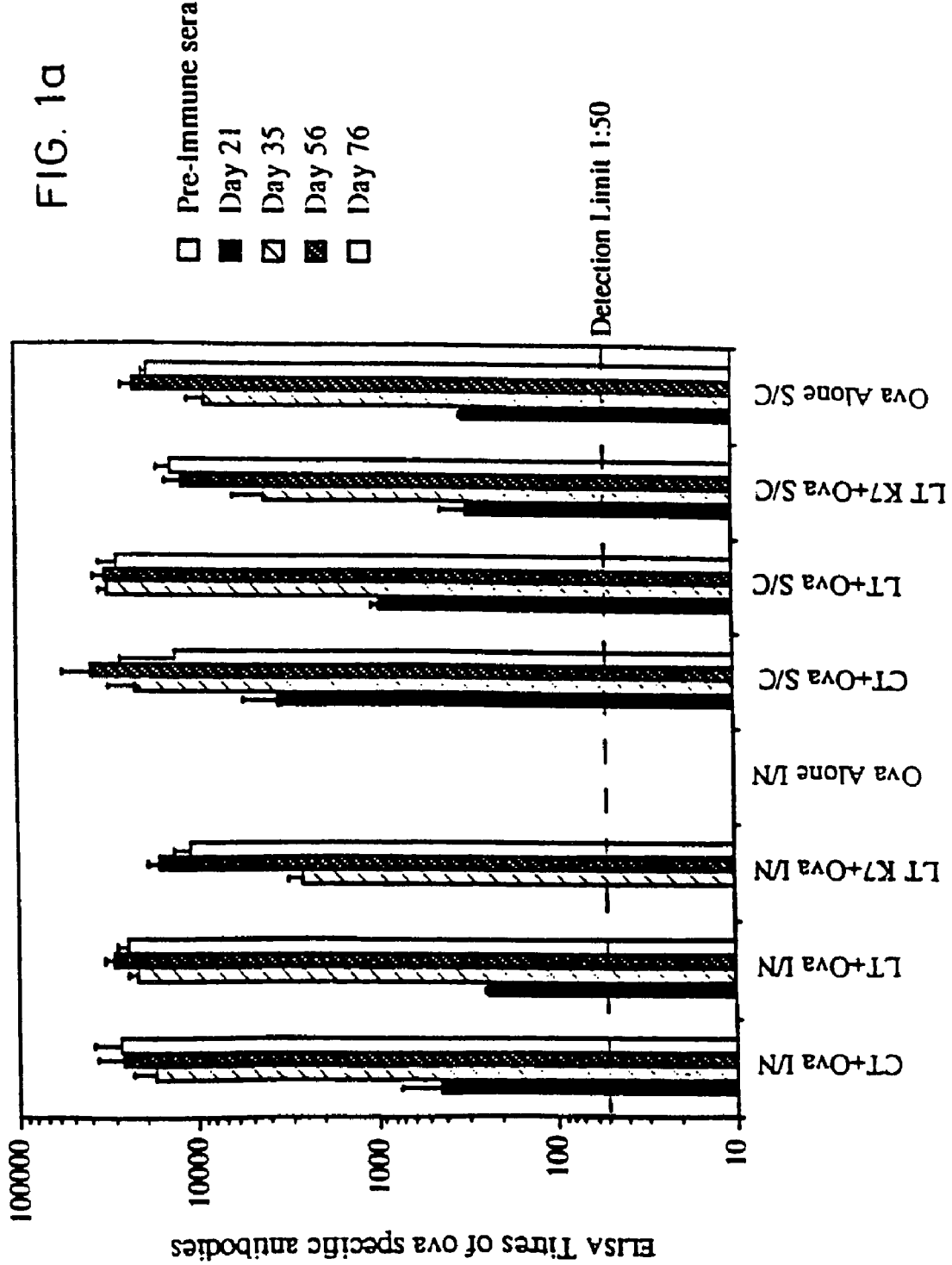
FIG. 1a shows the titre of total ovalbumin specific antibody in BALB/c mice immunised i/n or s/c with either ovalbumin alone or ovalbumin together with toxin derivatives.

Site-directed mutagenesis was used to replace the arginine residue at position seven of the A subunit of LT with lysine in order to construct a non-toxic LT mutant that could still assemble as a holotoxin with cell binding activity. The mutant protein, named LTK7, was purified and tested for ADP-ribosyltransferase and toxic activity in several assays. LTK7 was still able to bind GM1 ganglioside receptor but showed a complete loss of enzymatic activity, in agreement with published data (Lobet et al., Infect. Immun. 1991; 59:2870-2879). Further, LTK7 was inactive in the mouse ileal loop assay and in vitro on Y1 cells, even when a dose equivalent to $10^7$ toxic units of wild-type LT was tested (Table 1).

In vivo and in vitro Properties of LT and of LT K-7 Mutant

TABLE 1

|  | LT | LT-K7 | LT/LTK7 |
| --- | --- | --- | --- |
| Codon in position 7 of the A subunit | CGT | AAG | — |
| Aminoacid in position 7 of the A subunit | Arg | Lys | — |
| ADP-ribosyltransferase activity of the A subunit | 0.06 μg | >>20 μg | <<$3.10^{-3}$* |
| In vivo in mouse ileal loop | 10 μg | >>500 μg/ mouse | <<0.02** |
| In vitro toxicity on Y1 cells | 10 pg/ml | >>100 μg/ml | <<$10^{-7}$** |
| Binding to eukaryotic | + | + | 1 |

*Data published by Lobet et al. and confirmed in this study
**This study
>>Means that LT-K7 was still enzymatically inactive or non toxic when the highest concentration shown in the table was tested.
<<Indicates that the real difference is higher than the number shown which represents the difference tested.

The ability of LTK7 to act as a mucosal adjuvant was assessed in mice. Mice were separated into groups and immunised using ovalbumin as a reporter antigen. Animals were immunised intranasally (i/n) or subcutaneously (s/c) using 10 μg of ovalbumin alone or ovalbumin mixed with either 1 μg CT, LT or LTK7. Mice were split into four groups of six mice. Four mice from each group were lightly anaesthetised and immunised with either 10 μg of ovalbumin or 10 μg of ovalbumin with 10 μg of toxins, delivered in a total volume of 30 μl. The remaining two mice were immunised with the same amount of proteins s/c in a total volume of 100 μl. Proteins given subcut were first adsorbed to 2% $Al(OH)_3$.

Animals were immunised on days 1, 22, 36 and 61. Sample bleeds of 100 μl were collected on day 0, 21, 35, 56 and on day 76 animals were culled by cardiac puncture.

Quantitation of antibody was estimated by ELISA. For estimation of ovalbumin-specific antibodies, 96-well EIA plates (costar) were coated overnight with 60 μg/ml of ovalbumin. Measurement of toxin-specific antibodies was performed using a GM1 capture ELISA. Toxin-specific antibodies were measured against the antigen used in the immunisations. No single toxin was used in the measurements of toxin-specific antibody from each group, and as such the titres between these groups can not be compared directly.

Sera from each group were pooled from four and two mice respectively. Samples were prepared in duplicate from a dilution of 1:50. Absorbences were read at 450 nm using the kineticalc version 2.13 programme (Biotek instruments). This programme calculates the rate of change of substrate over thirty time points ten seconds apart.

ELISA titres of antibody were measured arbitrarily as the dilution of serum which gave half the maximal absorbence at 450 nm. Sera which failed to show absorbence at 450 nm 2.5 times greater than that observed with the equivalent preimmune sera were considered negative. Results shown in FIGS. 1a and 1b represent the mean titre values from duplicate wells from one experiment. No significant levels of antibodies to ovalbumin above background were detected in the serum of mice immunised i/n with ovalbumin alone although mice immunised s/c efficiently sero-converted. Mice receiving ovalbumin along with either CT or LT i/n contained very high levels of anti-ovalbumin antibodies in their sera. These were equivalent to those observed when mice immunised s/c. Mice that received ovalbumin with LTK7 also showed very high levels of antibodies to ovalbumin.

The levels of anti-toxoid responses in these same groups are shown in FIG. 1b. All mice, including those immunised with the mutant toxin, developed high levels of antibodies to these toxin in their sera.

Figure 2I:
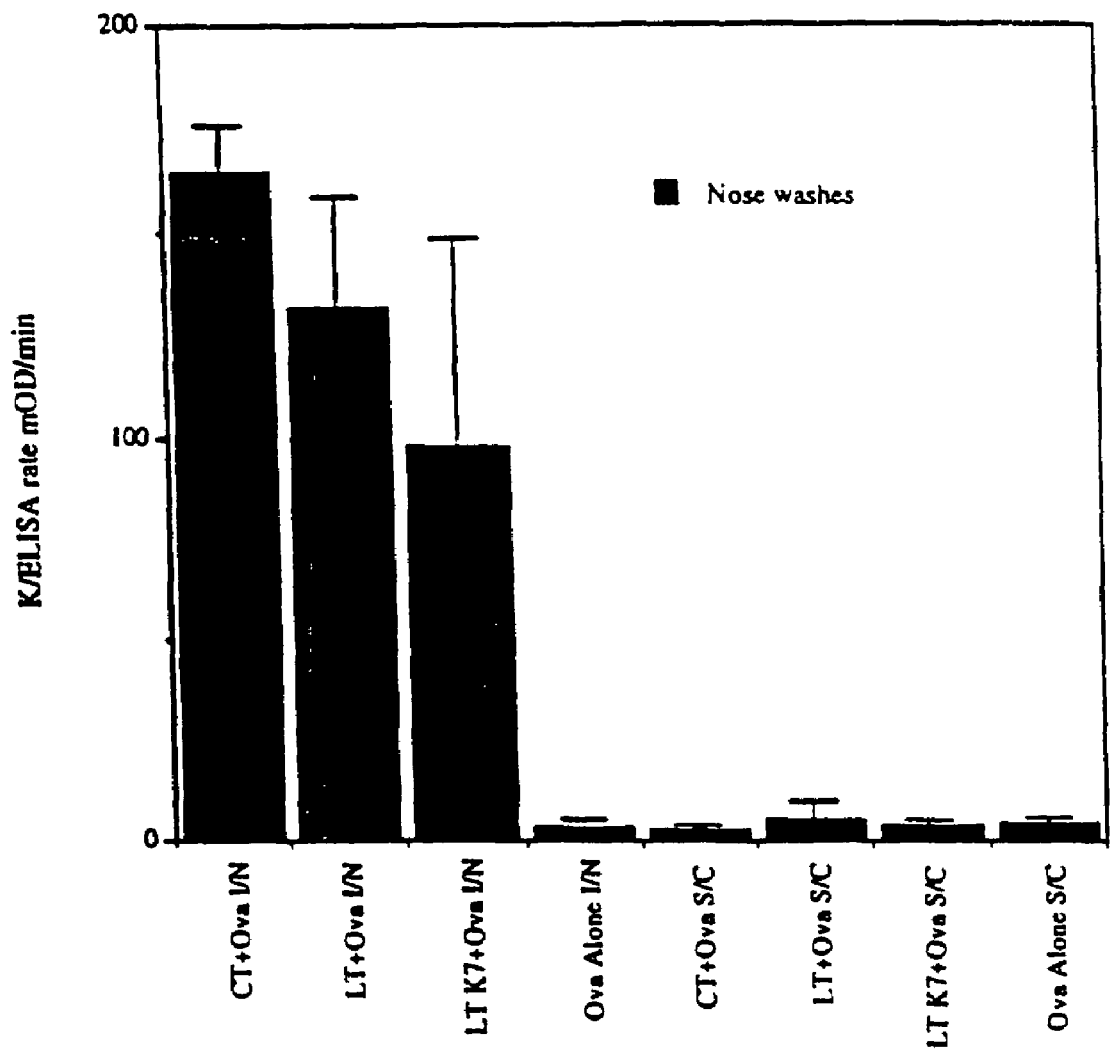
FIG. 2 shows a measurement of ovalbumin-specific IgA in nasal and lung lavages of mice injected as in FIG. 1.
Figure 2:
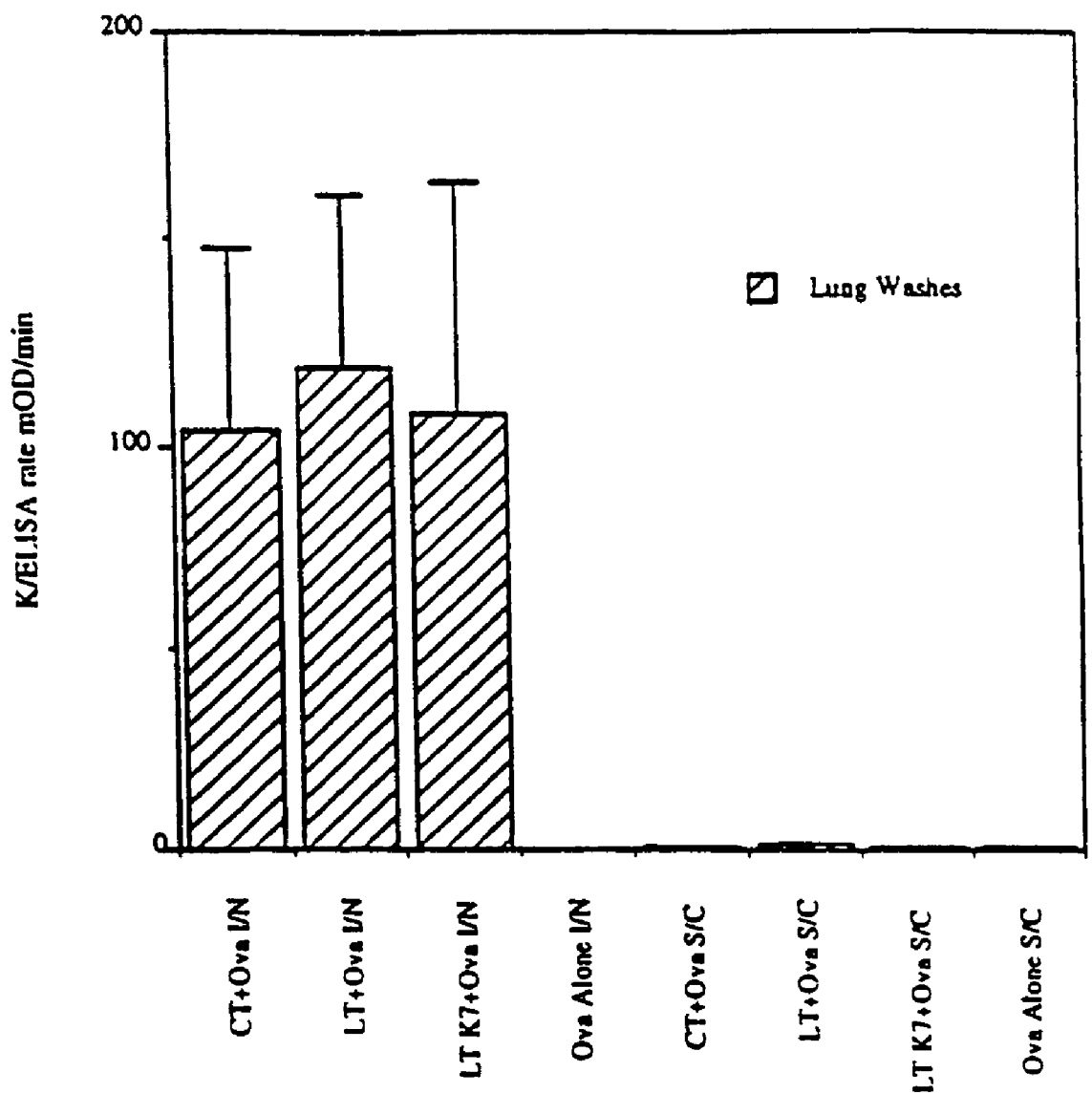

The local secretory antibody levels to ovalbumin were measured using both lung and nose washings (FIG. 2). In brief animals were culled by cardiac puncture and dissected so that the trachea was exposed. An ultra-thin pipette was then inserted into a small nick in the trachea. Lung washes were collected by repeated flushing and aspiration of 1.5 ml of 0.1% bovine serum albumin (Sigma), in PBS, into the lungs. Nose washes were collected by flushing 1 ml of 0.1% BSA in PBS through the nasal cavity.

Ovalbumin-specific IgA antibodies were measured by ELISA using an anti-mouse alpha-chain-specific conjugate antibody (Serotec). Samples were prepared from individual animals and columns in this figure represent the mean rate of change of substrate, using kineticalc, for four and two mice immunised i/n and s/c respectively. The figures are constructed using the raw absorbence data at a dilution of 1:3 with respect to lung washes. These correspond to titres of between 1:2 and 1:6 for nose washes and between 1:70 and 1:120 for lung washes. These titres were calculated using the method described above. Mice immunised s/c or i/n with ovalbumin alone contained no detectable ovalbumin-specific IgA in the washings sampled. All individual mice immunised with ovalbumin in combination with CT, LT or LTK7, showed detectable levels of anti-ovalbumin IgA. Thus both a local and systemic anti-ovalbumin response are detectable in these animals.

Figure 3:
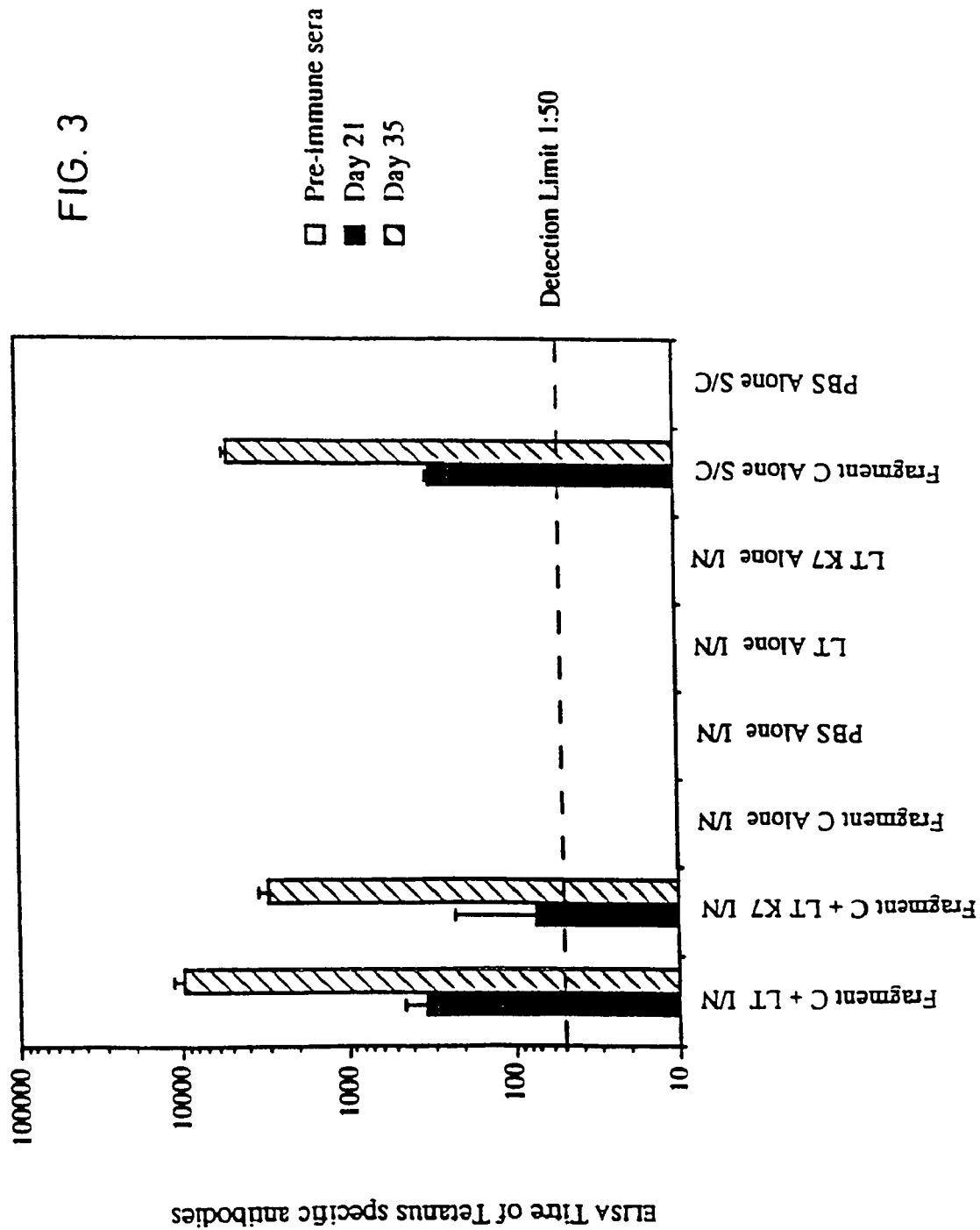
FIG. 3 shows the presence of tetanus toxoid-specific antibodies in the serum of BALB/c mice immunised i/n or s/c with tetanus toxin fragment C alone or together with toxin derivatives.

In the face of these encouraging experiments with ovalbumin the immunisation was repeated using Fragment C, a 50,000 dalton, non-toxic portion of tetanus toxin which had been expressed in and purified from the yeast *Pichia pastoris*. Mice were immunised either s/c or i/n with Fragment C alone or mixed with individual samples of either LT or LTK7. Mice were separated into four groups of ten mice and four groups of five mice. Ten mice were immunised i/n with a) 10 µg of fragment C alone; b) 10 µg of fragment C+1 µg of LT; C) 10 µg of fragment C+1 µg of LTK7 and d) PBS only, all in a final volume of 30 µl. Five mice were immunised i/n with a) 1 µg of LT and b) 1 µg of LTK7. The remaining two groups of mice were immunised s/c with either no protein or 10 µg of fragment C in a dose volume of 100 µl. These vaccines were prepared as described in FIG. 1. Animals were immunised on day 1 and 22. Sample bleeds of 10 µl were collected on day 0, 21 and 35. Fragment C-specific antibodies were measured by ELISA using tetanus toxid (10 µg/ml) as the coating antigen. Sera from each group were pooled. Samples were prepared in duplicate from a dilution of 1:50. ELISA titres were calculated as described above. Mice immunised s/c with Fragment C efficiently sero-converted producing high levels of anti-Fragment C antibodies (FIG. 3). Mice immunised i/n with Fragment C alone showed no significant sero-conversion. However mice immunised with Fragment C combined with LT or LTK7 showed high levels of anti Fragment C antibodies in their sera (FIG. 3). Since mice that sero-convert to Fragment C can be protected against toxin challenge the groups were challenged with active tetanus toxin. All mice immunised s/c with Fragment C alone were protected whereas all mice immunised i/n were highly susceptible. All mice i/n immunised with Fragment C combined with either LT or LTK7 survived the challenge (Table 2).

TABLE 2

|  | Serum anti-Fragment C | Deaths |
| --- | --- | --- |
| LT | --- | 10/10 |
| LTK7 | --- | 10/10 |
| LTK7 + Fragment C | ++ | 0/10 |
| Lt + Fragment C | ++++ | 0/10 |
| Fragment C | +/− | 10/10 |

The titre of anti-Fragment C antibodies in the serum of mice was on average about 1/3,000 in mice vaccinated with the K7 mutant + Fragment C and 1/12,000 for LT + Fragment C.

These experiments show that protective immunity against tetanus can be achieved using a non-toxic LT mutant as adjuvant and that mucosal immunisation with this molecule can generate both local secretory and systemic immune response to the toxin and co-administered bystander antigens.

The invention claimed is:

1. A pharmaceutical composition comprising a non-toxic mucosal adjuvant in admixture with an antigen, wherein
   (i) the non-toxic mucosal adjuvant comprises a detoxified mutant A subunit of a cholera toxin (CT) or an *E. coli* heat labile toxin (LT1 or LT2);
   (ii) said non-toxic mutant comprises one or more amino acid substitutions as compared to wild-type sequence of said toxin, and
   (iii) said mucosal adjuvant is not said antigen.

2. The composition according to claim 1, wherein the non-toxic mucosal adjuvant is LTK7.

3. A method for the prevention or treatment of a disease in a subject comprising administering to the subject an immunologically effective dose of an antigen adjuvanted with a non-toxic mutant as defined in claim 1 by contacting a mucosal surface of the subject with said adjuvanted antigen.

4. A method according to claim 3, comprising administration of a composition according to claim 1.

5. A method according to claim 4, wherein the adjuvanted antigen is administered orally or intranasally.

6. The method of claim 3, wherein the non-toxic mucosal adjuvant and a second antigen are administered simultaneously and separately or sequentially.

7. The method of claim 3, wherein the non-toxic mucosal adjuvant and a second antigen are administered simultaneously and are combined in a single vehicle, carrier or particle.

* * * * *